(12) United States Patent
Hartley et al.

(10) Patent No.: US 8,876,879 B2
(45) Date of Patent: Nov. 4, 2014

(54) INTRODUCER

(75) Inventors: David Ernest Hartley, Wannanup (AU); Werner Dieter Ducke, Greenwood (AU); Erik E. Rasmussen, Slagelse (DK)

(73) Assignee: Cook Medical Technologies LLC, Bloomington, IN (US)

( * ) Notice: Subject to any disclaimer, the term of this patent is extended or adjusted under 35 U.S.C. 154(b) by 1003 days.

(21) Appl. No.: 12/995,286

(22) PCT Filed: Jun. 4, 2009

(86) PCT No.: PCT/US2009/003393
§ 371 (c)(1),
(2), (4) Date: Feb. 14, 2011

(87) PCT Pub. No.: WO2009/148602
PCT Pub. Date: Dec. 10, 2009

(65) Prior Publication Data
US 2011/0144735 A1   Jun. 16, 2011

Related U.S. Application Data

(60) Provisional application No. 61/130,952, filed on Jun. 4, 2008.

(51) Int. Cl.
*A61F 2/06* (2013.01)
*A61F 2/966* (2013.01)
*A61F 2/07* (2013.01)
*A61F 2/95* (2013.01)

(52) U.S. Cl.
CPC . *A61F 2/966* (2013.01); *A61F 2/07* (2013.01); *A61F 2002/9511* (2013.01); *A61F 2/95* (2013.01); *A61F 2002/9665* (2013.01)
USPC .......................................... 623/1.11

(58) Field of Classification Search
CPC .......... A61F 2/95; A61F 2/962; A61F 2/9511
USPC ........ 623/1.11, 108, 153, 191, 192, 194, 198, 623/1.23
See application file for complete search history.

(56) References Cited

U.S. PATENT DOCUMENTS

2006/0004433 A1* 1/2006 Greenberg et al. .......... 623/1.11
2007/0186933 A1* 8/2007 Domingo et al. ........ 128/207.15

FOREIGN PATENT DOCUMENTS

EP    1 369 098       12/2003
EP    1 923 024    *  5/2008
(Continued)

OTHER PUBLICATIONS

International Search Report and Written Opinion for PCT/US2009/003393 mailed Aug. 21, 2009, 14 pgs.

(Continued)

*Primary Examiner* — Darwin Erezo
*Assistant Examiner* — Lindsey Bachman
(74) *Attorney, Agent, or Firm* — Brinks Gilson & Lione

(57) ABSTRACT

A stent graft introducer (1) has a distally opening capsule (5) on a nose cone dilator (3) and a plug device (17; 53) in the capsule. The plug device (17; 53) is movable longitudinally within the capsule (5) to move to a distal end (7) of the capsule (5) to extend from the capsule (5) whereby to provide a smooth transition from the otherwise distal opening (7) of the capsule (5) to enable retraction of the nose cone dilator (3) through a deployed stent graft (35). The capsule (5) includes an in-turned distal end (7) and the plug device (17; 53) has a proximal shoulder (25) whereby to prevent the plug device (17; 53) from being completely withdrawn from the capsule (5). The plug device (17; 53) has a distal linearly tapered surface (27) or a distally facing bullet shaped surface (57). There can be an arrangement (72; 80) to prevent subsequent retraction of the plug device (53; 17).

15 Claims, 6 Drawing Sheets

(56) References Cited

FOREIGN PATENT DOCUMENTS

| WO | WO 99/65418 | * 12/1999 |
| WO | WO 2005/037142 | 4/2005 |

OTHER PUBLICATIONS

International Preliminary Report on Patentabiltiy for PCT/US2009/003393 issued Dec. 6, 2010, 7 pgs.
Patent Examination Report No. 1 for Australian Patent Application No. 2009255608 issued Dec. 19, 2012, 4 pgs.
Response to Patent Examination Report No. 1 for Australian Patent Application No. 2009255608 filed Feb. 25, 2013, 3 pgs.
Patent Examination Report No. 2 for Australian Patent Application No. 2009255608 issued Feb. 28, 2013, 4 pgs.
Response to Patent Examination Report No. 2 for Australian Patent Application No. 2009255608 filed May 13, 2013, 2 pgs.
Patent Examination Report No. 3 for Australian Patent Application No. 2009255608 issued Jun. 13, 2013, 3 pgs.
Response to Patent Examination Report No. 3 for Australian Patent Application No. 2009255608 filed Aug. 15, 2013, 4 pgs.
Office Action for Japanese Patent Application 2011-512474 dated Dec. 10, 2012, 5 pgs. including English translation.

* cited by examiner

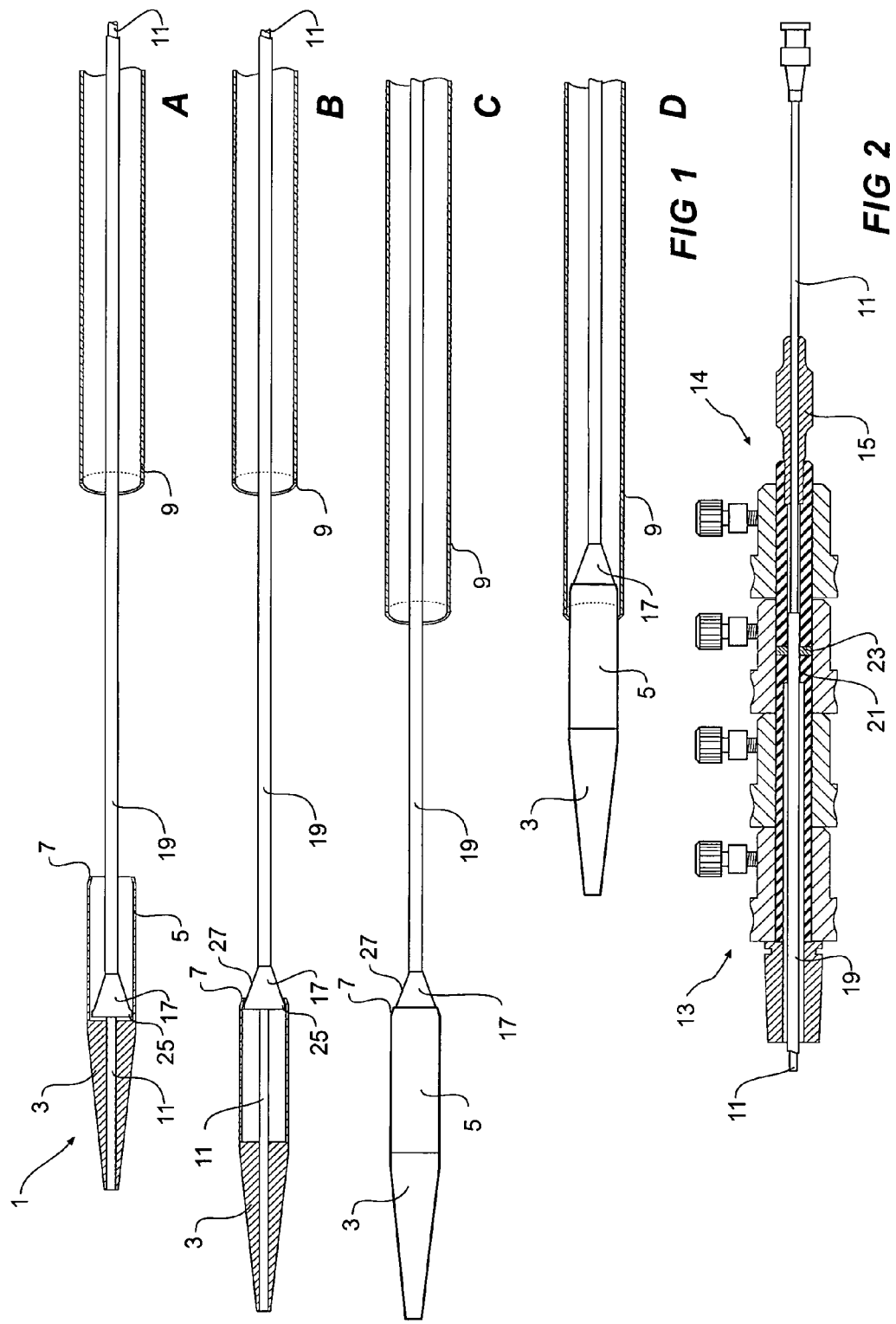

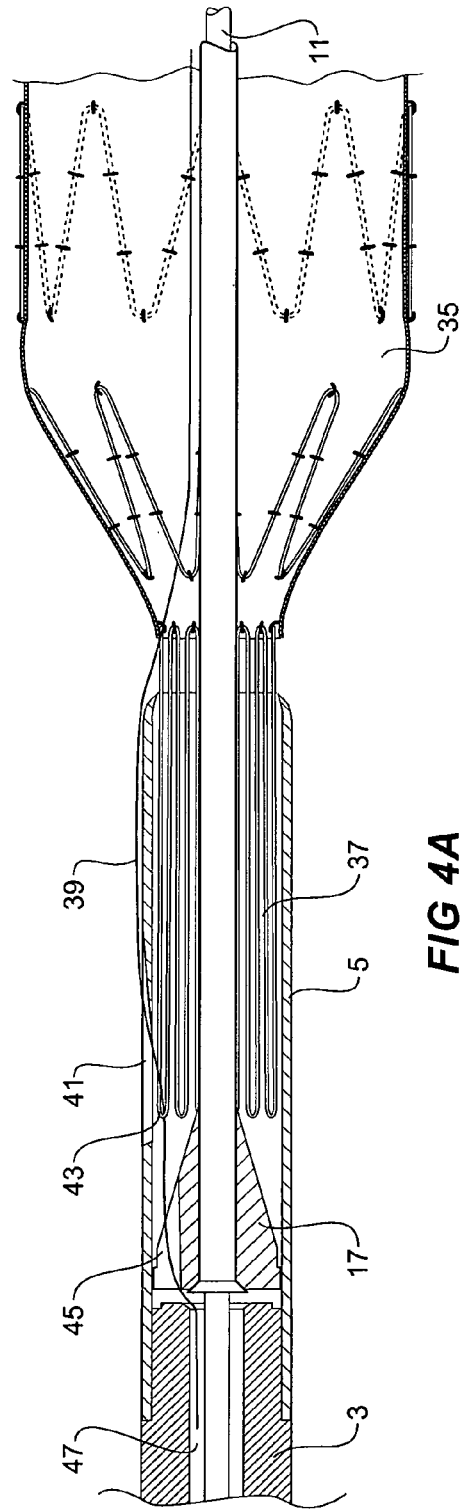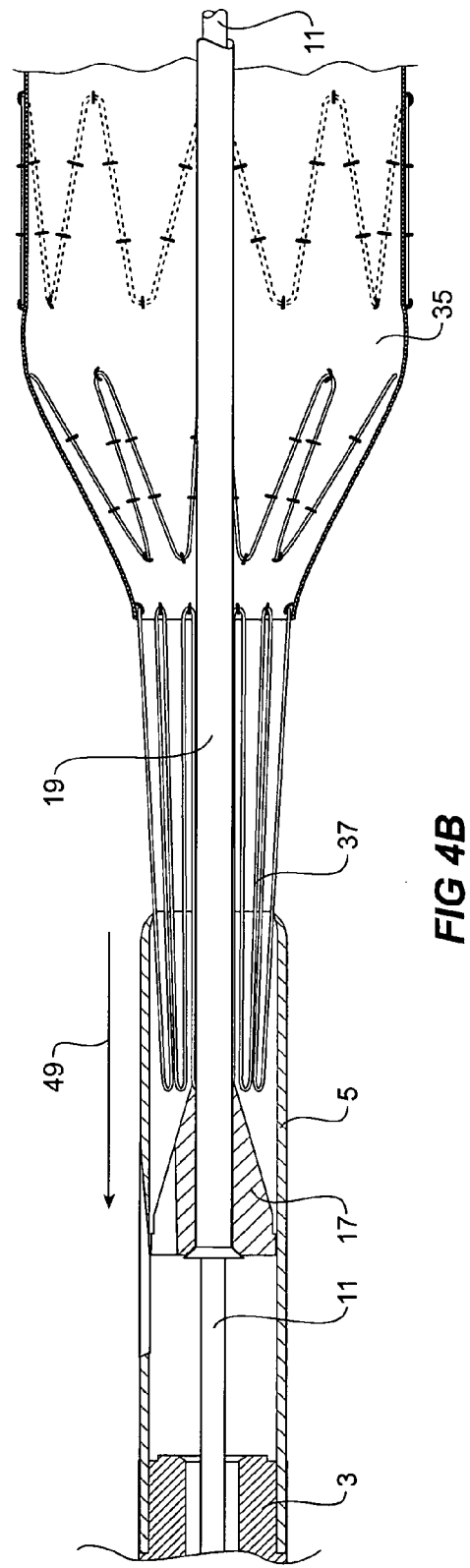

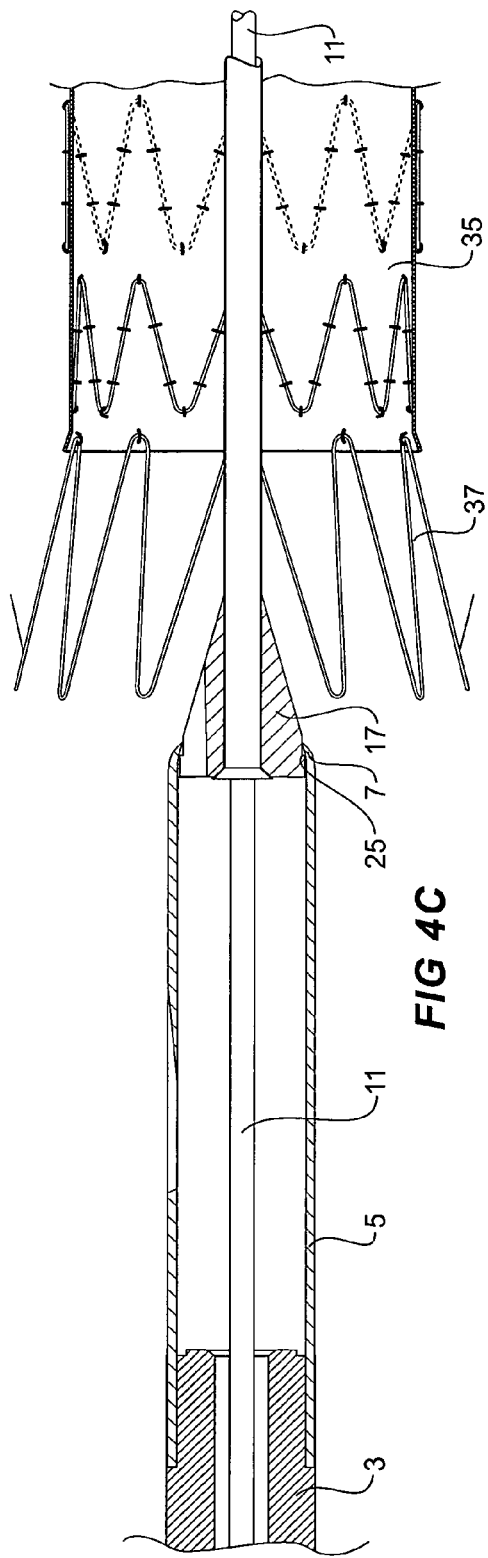
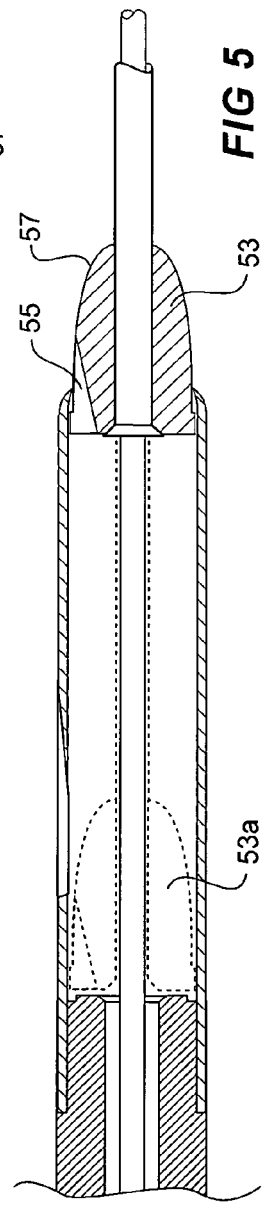
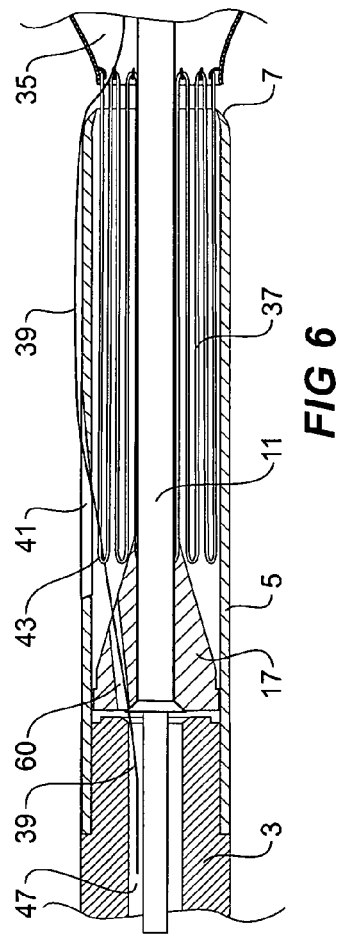

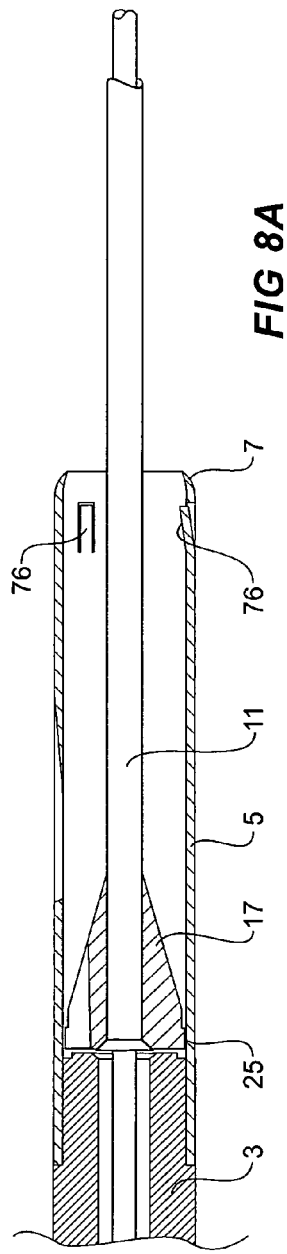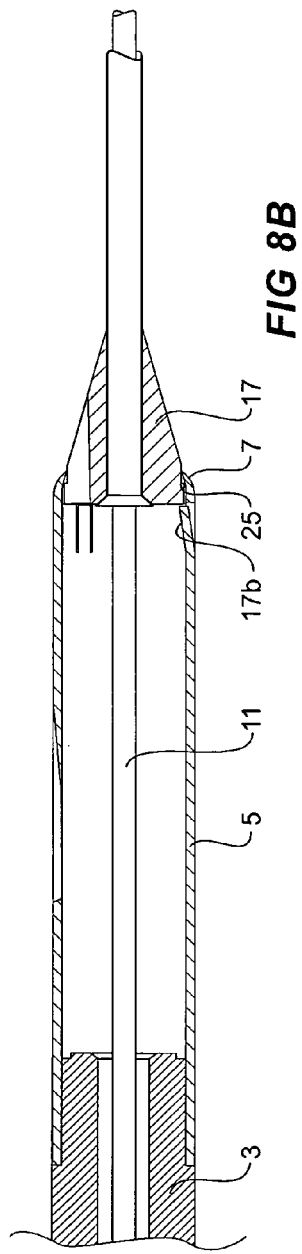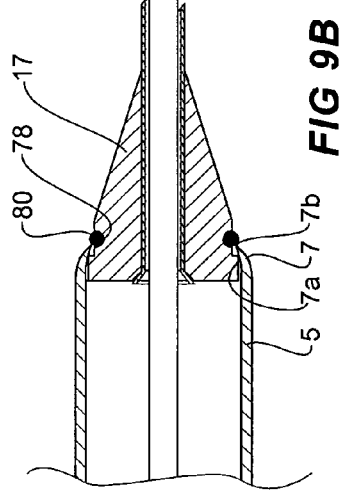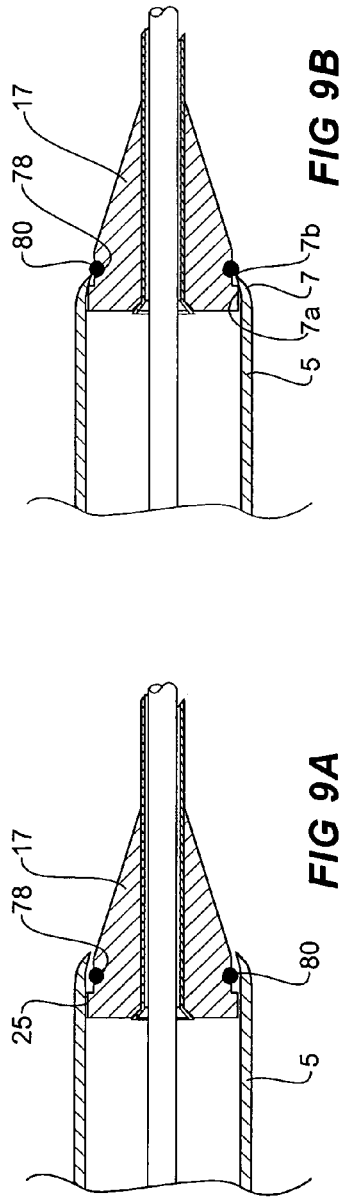

INTRODUCER

RELATED APPLICATIONS

The present patent document is a §371 filing based on PCT Application Serial No. PCT/US2009/003393, filed Jun. 4, 2009 (and published as WO 2009/148602 A1 on Dec. 10, 2009), designating the United States and published in English, which claims the benefit of the filing date under 35 U.S.C. §119(e) of Provisional U.S. Patent Application Ser. No. 61/130,952, filed Jun. 4, 2008. All of the foregoing applications are hereby incorporated by reference in their entirety.

TECHNICAL FIELD

This invention relates to a medical device and more particularly to a medical device used for deployment of an intraluminal graft or stent graft, otherwise referred to as an introducer or a stent graft introducer. In particular, this invention relates to a top cap retrieval arrangement.

BACKGROUND ART

In the deployment of a graft or stent graft into the human or animal body via intraluminal techniques a deployment device is used to introduce the graft into a lumen of the body and, after the graft has been deployed and expanded within the lumen, the introducer needs to be retracted.

One form of introducer uses a proximal nose cone with a distally facing capsule to encompass an exposed stent and barbs on the exposed stent of a stent graft during introduction and, after the stent graft has been released and the capsule has been removed from the exposed stent, the capsule along with the introducer must be withdrawn. The capsule, however, has a distally facing opening with an edge surrounding it and this edge can engage with stents of the just introduced stent graft and cause problems with dislodging the stent graft from its position on the wall of the lumen. Similarly, an introducer often has a sheath which is used to constrain a stent or stent graft during delivery and this sheath is withdrawn from the stent or stent graft to release the stent or stent graft. This sheath has a proximally facing opening and a surrounding edge so if the sheath is advanced to meet the distally facing capsule then that edge may engage with stents of the just introduced stent graft and cause problems with dislodging the stent graft from its position on the wall of the lumen. It is desirable to engage the sheath with the capsule before withdrawal and hence some way of preventing the edges as discussed above from dislodging the stent graft is desirable.

It is the object of this invention to address one or more of the above problems or at least to provide the practitioner in the field with a useful alternative device.

Throughout this specification the term distal with respect to a portion of the aorta, a deployment device or a prosthesis means the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

DISCLOSURE OF THE INVENTION

According to an aspect of the present invention, there is provided an introducer comprising a guide wire cannula extending from a handle to a nose cone dilator at a proximal end of the guide wire cannula, a distally opening capsule on the nose cone dilator, a plug device in the capsule, the plug device being mounted onto the guide wire cannula and being movable longitudinally with respect to the guide wire cannula, whereby movement of the plug device to a distal end of the capsule to extend from the capsule provides a smooth transition from the otherwise distal opening of the capsule to enable retraction of the nose cone dilator through a deployed stent.

In one form, an embodiment of a stent graft introducer comprises a guide wire cannula extending from a handle to a nose cone dilator at a proximal end of the guide wire cannula, a distally opening capsule on the nose cone dilator, a plug device in the capsule, the plug device being mounted onto the guide wire cannula and being movable longitudinally with respect to the guide wire cannula, whereby movement of the tapered plug device to a distal end of the capsule to extend from the capsule provides a smooth transition from the otherwise distal opening of the capsule to enable retraction of the nose cone dilator through a deployed stent.

Preferably there is included a plug catheter coaxially on the guide wire catheter and movable longitudinally with respect to the guide wire catheter, the plug catheter being fixed to the plug device whereby movement of the plug catheter enables movement of the plug device. Preferably the plug catheter coaxially on the guide wire catheter comprises a thin walled plastics material.

Preferably the capsule includes an in-turned distal end and the plug device comprises a proximal shoulder whereby to prevent the plug device from being completely withdrawn from the capsule.

Preferably the plug device comprises a distal linearly tapered surface. Alternatively the plug device comprises a distally facing bullet shaped surface.

Preferably the plug device comprises a spring arrangement to move the plug device from a rest position to the distal end of the capsule.

There can be further included an anti-return arrangement associated with the capsule or with the plug device. The anti-return arrangement associated with the capsule can comprises at least one engagement tab extending into the capsule whereby the plug device can pass the at least one engagement tab when moving in a distal direction but cannot pass the at least one engagement tab when moving in a proximal direction. The anti-return arrangement associated with the plug device can comprise an O-ring around the plug device which can pass out of the capsule but cannot re-enter the capsule.

In another embodiment a stent graft introducer comprises a handle, a guide wire catheter extending from the handle to a nose cone dilator at a proximal end of the guide wire catheter, the guide wire catheter being movable longitudinally with respect to the handle, a distally opening capsule on the nose cone dilator, a plug device in the capsule, the plug device being mounted onto the guide wire catheter and movable longitudinally with respect to the guide wire catheter, a plug catheter coaxially on the guide wire catheter and movable longitudinally with respect to the guide wire catheter, the plug catheter being fixed to the plug device at a proximal end and to the handle at a distal end whereby movement of the guide wire catheter with respect to the handle moves the tapered plug device with respect to the distally opening capsule such that the tapered plug device can move to a distal end of the capsule to extend from the capsule whereby to provide a smooth transition from the otherwise distal opening of the capsule to enable retraction of the nose cone dilator through a deployed stent graft.

Preferably the capsule includes an in-turned distal end and the plug device comprises a proximal shoulder whereby to prevent the plug device from being completely withdrawn from the capsule.

The plug device is generally narrower at its distal end than at its widest point generally towards its proximal end, and has a shape that provides a smooth transaction from its widest point to its distal end. This could be generally described as being tapered. For example, the plug device may comprise a distal linearly tapered surface or a distally facing bullet shaped surface.

Preferably the plug catheter coaxially on the guide wire catheter comprises a thin walled plastics material. The thin walled plastics material can comprise polyetheretherketone (PEEK).

The fixing of the plug catheter to the handle at a distal end can comprise an adhesive.

The plug device can comprise a longitudinal groove or aperture whereby to allow a trigger wire to pass therethrough.

There can be further included an anti-return arrangement associated with the capsule or with the plug device. The anti-return arrangement associated with the capsule can comprises at least one engagement tab extending into the capsule whereby the plug device can pass the at least one engagement tab when moving in a distal direction but cannot pass the at least one engagement tab when moving in a proximal direction. The anti-return arrangement associated with the plug device can comprise an O-ring around the plug device which can pass out of the capsule but cannot re-enter the capsule.

It will be seen that the above-described introducer includes an arrangement that, more or less automatically, as the nose cone dilator and capsule of an introduction device is advanced proximally to release an exposed stent of a stent graft from the capsule, the plug device moves to the distal end of the capsule to provided a smooth transition to the capsule for withdrawal of the nose cone dilator and capsule through the deployed stent graft. The nose cone and capsule can be retracted to the sheath so that the introducer as a whole can be retracted without causing problems such as those outlined above with respect to the prior art.

BRIEF DESCRIPTION OF THE DRAWINGS

Preferred embodiments are now described by way of example only and with reference to the accompanying drawings in which:

FIGS. 1A to 1D show a schematic view of one embodiment of top cap retrieval device at various stages of operation;

FIG. 2 shows a handle portion of a stent graft delivery device;

FIGS. 4A to 4C shows in detailed cross section a portion of a stent graft delivery device; and FIG. 5 shows in detailed cross section a portion of a stent graft delivery device;

FIG. 6 shows in detailed cross section a portion of a stent graft delivery device;

FIGS. 8A and 8B show an embodiment of tapered retrieval plug; and

FIGS. 9A and 9B show an embodiment of tapered retrieval plug.

DESCRIPTION OF THE PREFERRED EMBODIMENTS

Figure 3:
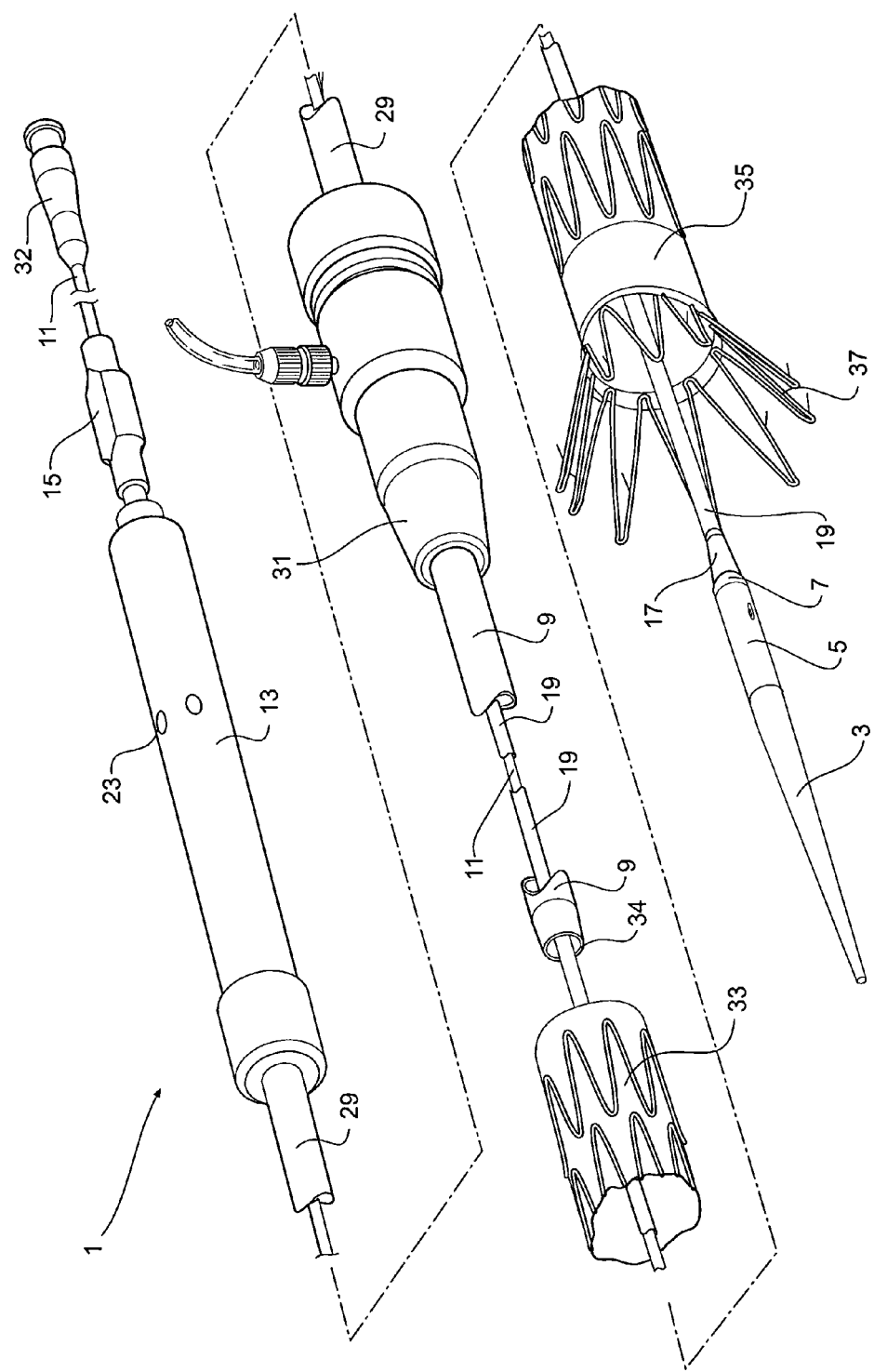
FIG. 3 shows a stent graft delivery device with the plug device in a position to facilitate withdrawal of the nose cone dilator.

Now looking more closely at the drawings and in particular FIGS. 1A to 1D which show a schematic view of one embodiment of a top cap retrieval device in various stages of operation and FIG. 2 which shows a handle portion of a stent graft delivery device incorporating part of the top cap retrieval device.

A stent graft delivery device 1 has a nose cone dilator 3. At the distal end of the nose cone dilator 3 is a distally opening capsule 5 for the receipt of an exposed stent of a stent graft. For clarity the exposed stent is not shown in this drawing but is shown in FIG. 4A below. The capsule 5 has a slightly radially in-turned distal end 7. This has two purposes. The first is to assist with engagement of a sheath 9 of the delivery device when the sheath 9 is advanced to the nose cone dilator 3. The second is to prevent complete withdrawal of the plug device (see below) from the capsule 5 as will be discussed below. The delivery device 1 has a guide wire catheter 11 (also referred to herein as a guide wire cannula) which passes through and is fastened to the nose cone dilator 3 at its proximal end and passes through a handle 13 (see FIG. 2) of the delivery device 1. A pin vice arrangement 15 at the distal end 14 of the handle 13 locks movement of the guide wire catheter 11 with respect to the handle 13 and can be loosened to allow relative motion between these components as discussed below.

Within the capsule 5 is a plug device 17, which in this embodiment is tapered. The plug device fits coaxially around the guide wire catheter 11 and can move longitudinally along the guide wire catheter. A plug catheter 19 is mounted coaxially around the guide wire catheter 11 and can move longitudinally along the guide wire catheter. At its proximal end the plug catheter 19 is joined to the tapered plug device 17 and at its distal end the plug catheter 19 is joined to the handle at 21 by a suitable adhesive (see FIG. 2). For this purpose apertures 23 are provided into the handle and adhesive is applied through these apertures.

The tapered plug device 17 has an enlarged shoulder 25 at its proximal end. The shoulder is sized so that it is of greater diameter than the smallest part of the in-turned distal end 7 of the capsule 5. By this arrangement the tapered plug device 17 can move through the capsule 5 but cannot be fully removed from the capsule 5.

FIG. 1A shows the delivery device 1 (minus a stent graft) before the capsule 5 is advanced proximally to release an exposed stent on the stent graft. The tapered plug device 17 at this stage is at the proximal end of the capsule 5 and does not interfere with an exposed stent received in the capsule 5.

FIG. 1B shows the capsule 5 has been advanced proximally to release the exposed stent on the stent graft. The tapered plug device 17 at this stage is at the distal end 7 of the capsule 5 and a majority of the tapered plug device 17 extends from the capsule to provide a tapered surface 27. This has the effect of closing the distal opening of the capsule 5 and provides a smooth transition from the otherwise distal opening of the capsule 5 to enable retraction of the nose cone dilator 3 and capsule 5 through the deployed stent graft.

FIG. 1C shows the view of FIG. 1B but without the nose cone 3 and capsule 5 in cross-section. The smooth transition from the otherwise distal opening of the capsule 5 can be easily seen.

FIG. 1D shows the view of FIG. 1C with the nose cone dilator 3, the capsule 5 and the tapered plug device 17 all withdrawn into the sheath 9. To achieve this the pin vice 15 (see FIG. 2) is locked and the handle 13 is moved distally with respect to the sheath 9.

FIG. 3 shows a stent graft delivery device according to an embodiment of the present invention, with the plug device 17 in a position to facilitate withdrawal of the nose cone dilator 3. In FIG. 3 the same reference numerals are used for corresponding items to those of FIGS. 1A to 1D and FIG. 2.

The stent graft delivery device 1 has a handle 13 and from the handle 13 extends a delivery catheter 29 to a sheath manipulator 31 to which is connected the sheath 9. At this stage of delivery of the stent graft all of the trigger wire release devices which are depicted on the handle in FIG. 2 have been removed. The guide wire catheter 11 extends from a Luer lock connector 32 at the distal end of the device through the pin vice 15, handle 13 and delivery catheter 29 to the nose cone dilator 3 at the proximal end of the device 1. At the distal end of the nose cone dilator 3 is a distally opening capsule 5 with an in-turned distal end 7. Extending distally from the capsule 5 is a tapered plug device 17. The tapered plug device 17 is joined to a plug catheter 19 which is coaxial with the guide wire catheter 11 and can move with respect to the guide wire catheter 11. The plug catheter 19 extends back distally into the handle 13 and is fastened into the handle by adhesive passed through the aperture 23.

In this embodiment, the stent 35 is shown in its expanded state as it appears after release from the delivery device. The proximally extending exposed stent 37 would have been received within the capsule during delivery to the release site and the stent graft would have been constrained by the sheath 9 which, in turn, at that stage would have extended to the capsule 5.

It will be seen that by this arrangement the distally facing tapered surface 27 of the tapered plug device 17 presents a surface which will not engage with stents of the stent graft while the nose cone dilator, the capsule and the tapered plug device are all withdrawn into the proximal end 34 of the sheath 9 through the stent graft 35.

FIGS. 4A to 4C shows in detailed cross section a portion of a stent graft delivery device 1 according to an embodiment of the present invention. In FIGS. 4A to 4C the same reference numerals are used for corresponding items to those of FIGS. 1A to 1D, 2 and 3.

In FIG. 4A the exposed stent 37 is received into the capsule 5 and it is prevented from being prematurely removed from the capsule 5 by the use of a trigger wire 39 which passes through the stent graft 35 to outside the capsule 5 and then enters the capsule 5 through aperture 41 in the capsule wall. The trigger wire 39 then passes through one of the bends 43 of the exposed stent 37 and then past the tapered plug device 17 and into an aperture 47 in the nose cone dilator 3. To enable the trigger wire 39 to pass the tapered plug device 17 there is a longitudinal slot 45 in the plug device 17. It will be noted that at this stage the plug device 17 does not interfere with the retention of the exposed stent into the capsule.

In FIG. 4B the trigger wire 39 has been removed and the nose cone dilator 3 and capsule 5 have been advanced proximally by movement of the guide wire catheter 11 as indicated by the arrow 49. The exposed stent 37 is still partly retained in the capsule. The tapered plug device 17 has in effect moved towards the distal end 7 of the capsule 5.

In FIG. 4C the nose cone dilator 3 and capsule 5 have been advanced further proximally by movement of the guide wire catheter 11 until the exposed stent 37 has been released from the capsule 5. At this stage the tapered plug device 17 has moved so that it is mostly out of the capsule but that the enlarged shoulder 25 is still within the capsule 5 and is engaged against the in-turned edge 7 which prevents the tapered plug device 17 from being fully removed from the capsule 5. At this stage the nose cone dilator 3, the capsule 5 and the tapered plug device 17 can all be withdrawn together through the stent graft.

FIG. 5 shows in detailed cross section a portion of a stent graft delivery device according to another embodiment of the present invention. In this embodiment the plug device 53 has a surface shape of a distally facing bullet. The plug device 53 has a slot 55 to allow a trigger wire 39 to pass the plug device 53. The dotted lines indicate the position of the plug device 53 during introduction of the stent graft 35.

FIG. 6 shows in detailed cross section a portion of a stent graft delivery device according to an another embodiment of the present invention. In FIG. 6 the same reference numerals are used for corresponding items to those of FIG. 4A.

In FIG. 6 an exposed stent 37 of a stent graft 35 is received into the capsule 5 of a delivery device and the exposed stent is prevented from being prematurely removed from the capsule by the use of a trigger wire 39 which passes through the stent graft 35 to outside the capsule 5 and then enters the capsule 5 through aperture 41 in the capsule wall. The trigger wire 39 then passes through one of the bends 43 of the exposed stent 37 and then past the plug device 17 and into an aperture 47 in the nose cone dilator 3. To enable the trigger wire 39 to pass the plug device there is an aperture 60 in the plug device 17.

Figure 7A:
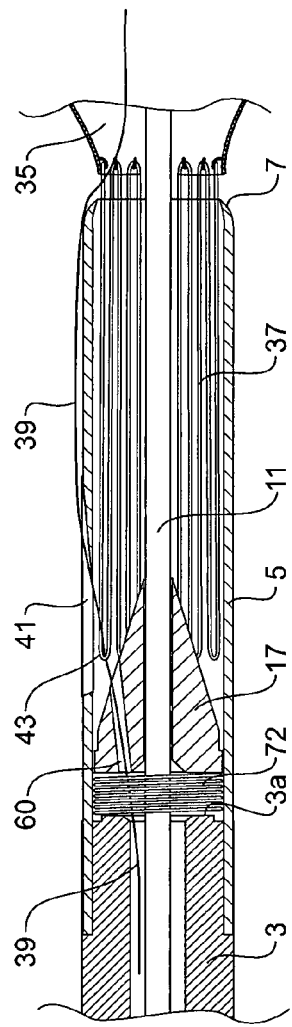
FIGS. 7A and 7B show an embodiment of tapered retrieval plug.
Figure 7B:
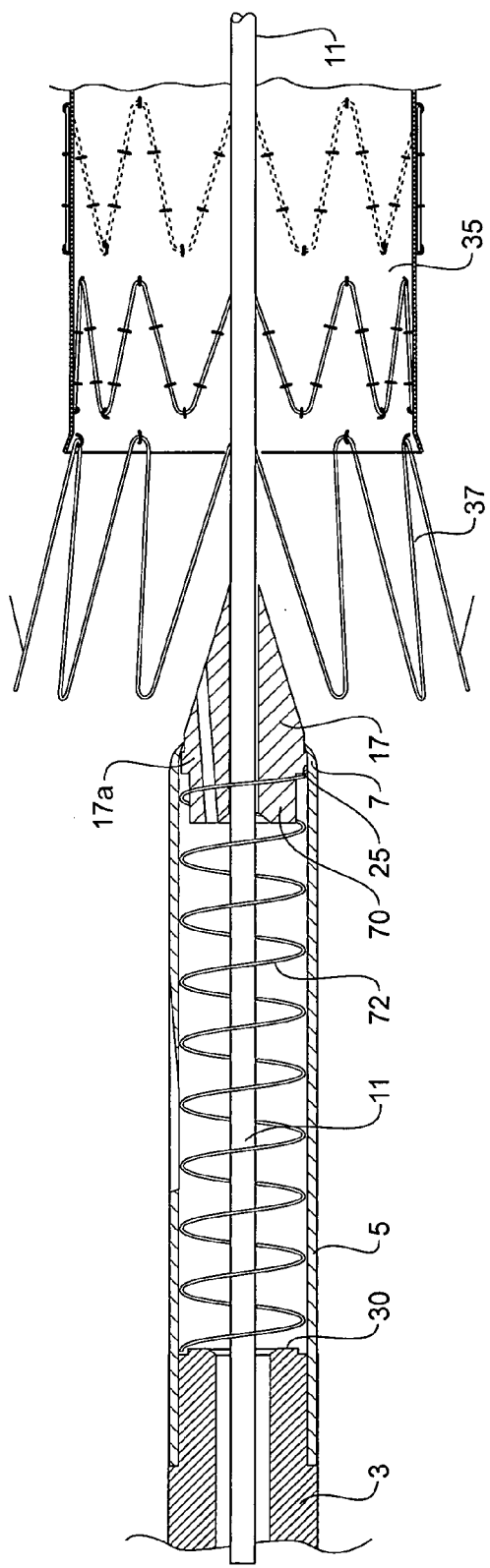

FIGS. 7A and 7B show another embodiment of the present invention. In this embodiment the same reference numeral are used for corresponding items as in the earlier embodiments.

In FIGS. 7A and 7B the retrieval plug 17 includes a cylindrical extension 70 at its proximal end 17a. A coil spring 72 is received over the cylindrical extension 70 and in the position shown in FIG. 7A the spring is compressed against the distal end 3a of the nose cone dilator 3. The spring 72 tends to push the retrieval plug 17 towards the open distal end 7 of the capsule 5 but is held in the retracted or proximal position by the exposed stent 37 of the stent graft 35. Other methods such as a trigger wire system can also be used to hold the retrieval plug 17 in the retracted position. For instance, the trigger wire 39 which prevents premature retraction of the exposed stent 37 may also hold the plug device 17 in the retracted position. As the exposed stent 37 is retracted from the capsule 5 by proximal movement of the nose cone dilator 3 the retrieval plug 17 follows the exposed stent 37 and moves to the open distal end 7 of the capsule 5 under the action of the spring 72.

Arrangements such as those shown in the following two embodiments may be used to prevent subsequent movement of the retrieval plug 17 back from the open distal end 7 of the capsule 5.

FIGS. 8A and 8B show an embodiment of the present invention. In this embodiment the same reference numeral are used for corresponding items as in the earlier embodiments.

In FIGS. 8A and 8B an arrangement is provided to prevent movement of the retrieval plug 17 back from the open end 7 of the capsule 5 after it has been moved to the open end 7 by whatever mechanism is used. In FIGS. 8A and 8B a number of tabs 76 are cut into the capsule 5 in the form of, in this embodiment a U-shape with open ends extending distally and bent inward slightly. During movement of the retrieval plug 17 to the distal end 7 of the capsule 5 the shoulder 25 on the retrieval plug 17 deflects the tabs 76 but after the retrieval plug 17 has passed the tabs 76 they deflect out (radially inwardly) and engage against the rear surface 17b of the retrieval plug 17 thereby preventing movement of the retrieval plug 17 back from the open end 7 of the capsule 5 after it has been moved to the open end 7. This provides an anti-return feature associated with the capsule 5.

FIGS. 9A and 9B show another embodiment of the present invention. In this embodiment the same reference numeral are used for corresponding items as in the earlier embodiments.

In FIGS. 9A and 9B an arrangement is provided to prevent movement of the retrieval plug 17 back from the open end 7 of the capsule 5 after it has been moved to the open end 7 by whatever mechanism is used. In this embodiment the retrieval plug 17 has a peripheral O-ring groove 78 distal of the shoulder 25 with a biocompatible material O-ring 80 received therein. The capsule 5 has in-turned distal edge 7 which prevents the tapered plug device 17 from being fully removed from the capsule 5. During the distal movement of the plug 17 the O-ring 80 is deflected radially inwards by the inner surface 7a of the in-turned edge 7 but once the O-ring 80 has passed the in-turned edge 7 it is engaged by the end 7b of the in-turned edge 7 and hence the plug device 17 cannot move in the proximal direction. This provides an anti-return feature associated with the plug device.

The skilled person will appreciate that features described in conjunction with the tapered plug device 17 may apply equally to the bullet-shaped plug device 53 as appropriate. In particular, the specific features described with respect to FIGS. 6 to 9, whilst illustrated with a tapered retrieval plug 17, could equally be used with retrieval plugs having different shapes. Where applicable, the features of the various embodiments may be combined as appropriate.

Throughout this specification various indications are given to the scope of the invention but the invention is not limited to any one of these but may reside in two or more combined together. The described embodiments are given for illustration and not for limitation.

The disclosures in U.S. Pat. No. 61/130,952 from which this application claims priority, and in the abstract accompanying this application are hereby incorporated by reference.

The invention claimed is:

1. An introducer comprising a guide wire cannula extending from a handle to a nose cone dilator at a proximal end of the guide wire cannula, a distally opening capsule on the nose cone dilator, a plug device in the capsule, the plug device being mounted onto the guide wire cannula and being movable longitudinally with respect to the guide wire cannula, whereby movement of the plug device to a distal end of the capsule to extend from the capsule provides a smooth transition from the otherwise distal opening of the capsule to enable retraction of the nose cone dilator through a deployed stent; and
an anti-return arrangement comprising at least one of:
at least one engagement tab extending into the capsule whereby the plug device can pass the at least one engagement tab when moving in a distal direction but cannot pass the at least one engagement tab when moving in a proximal direction; or
an O-ring secured around the plug device which can pass out of the capsule but cannot re-enter the capsule.

2. An introducer as claimed in claim 1, including a plug catheter coaxially on the guide wire cannula and movable longitudinally with respect to the guide wire cannula, the plug catheter being fixed to the plug device whereby movement of the plug catheter enables movement of the plug device.

3. An introducer as claimed in claim 2, wherein the plug catheter comprises a thin walled plastics material.

4. An introducer as claimed in claim 3, wherein the thin walled plastics material comprises polyetheretherketone (PEEK).

5. An introducer as claimed in claim 2, wherein the plug catheter is fixed to the handle at a distal end wherein the fixing of the plug catheter to the handle at a distal end comprises an adhesive.

6. An introducer as claimed in claim 1, wherein the capsule includes an in-turned distal end and the plug device comprises a proximal shoulder whereby to prevent the plug device from being completely withdrawn from the capsule.

7. An introducer as claimed in claim 1, wherein the plug device comprises a distal linearly tapered surface.

8. An introducer as claimed in claim 1, wherein the plug device comprises a distally facing bullet shaped surface.

9. An introducer as claimed in claim 1, wherein the plug device comprises a spring arrangement to move the plug device from a rest position to the distal end of the capsule.

10. An introducer as claimed in claim 1, wherein the plug device includes a longitudinal groove or aperture whereby to allow a trigger wire to pass therethrough.

11. An introducer as claimed in claim 1, including a stent or stent graft mounted thereon.

12. An introducer comprising:
a guide wire cannula extending from a handle to a nose cone dilator at a proximal end of the guide wire cannula;
a distally opening capsule on the nose cone dilator; and
a plug device in the capsule, the plug device being mounted onto the guide wire cannula and being movable longitudinally with respect to the guide wire cannula,
whereby movement of the plug device to a distal end of the capsule to extend from the capsule provides a smooth transition from the otherwise distal opening of the capsule to enable retraction of the nose cone dilator through a deployed stent, and
wherein the capsule includes an in-turned distal end and the plug device comprises a proximal shoulder whereby to permanently prevent the plug device from being completely withdrawn from the capsule.

13. The introducer as claimed in claim 12, further comprising a plug catheter coaxially on the guide wire cannula and movable longitudinally with respect to the guide wire cannula, the plug catheter being fixed to the plug device whereby movement of the plug catheter enables movement of the plug device.

14. An introducer comprising:
a guide wire cannula extending from a handle to a nose cone dilator at a proximal end of the guide wire cannula;
a distally opening capsule on the nose cone dilator; and
a plug device in the capsule, the plug device being mounted onto the guide wire cannula and being movable longitudinally with respect to the guide wire cannula,
whereby movement of the plug device to a distal end of the capsule to extend from the capsule provides a smooth transition from the otherwise distal opening of the capsule to enable retraction of the nose cone dilator through a deployed stent, and
wherein the plug device includes a longitudinal groove or aperture, which is at least partially spaced apart from a longitudinal axis of the plug device, to allow a trigger wire to pass therethrough; and
an anti-return arrangement comprising at least one engagement tab extending into the capsule whereby the plug device can pass the at least one engagement tab when moving in a distal direction but cannot pass the at least one engagement tab when moving in a proximal direction.

15. An introducer comprising:
a guide wire cannula extending from a handle to a nose cone dilator at a proximal end of the guide wire cannula;

a distally opening capsule on the nose cone dilator; and
a plug device in the capsule, the plug device being mounted onto the guide wire cannula and being movable longitudinally with respect to the guide wire cannula,
whereby movement of the plug device to a distal end of the capsule to extend from the capsule provides a smooth transition from the otherwise distal opening of the capsule to enable retraction of the nose cone dilator through a deployed stent, and
wherein the plug device includes a longitudinal groove or aperture, which is at least partially spaced apart from a longitudinal axis of the plug device, to allow trigger wire to pass through; and
an anti-return arrangement comprising an O-ring around the plug device which can pass out the capsule but cannot re-enter the capsule.

* * * * *

UNITED STATES PATENT AND TRADEMARK OFFICE
CERTIFICATE OF CORRECTION

PATENT NO.      : 8,876,879 B2
APPLICATION NO. : 12/995286
DATED           : November 4, 2014
INVENTOR(S)     : David Ernest Hartley et al.

Page 1 of 1

It is certified that error appears in the above-identified patent and that said Letters Patent is hereby corrected as shown below:

<u>In the Claims</u>

In column 9, claim 15, line 12, before "trigger wire" insert --a--.

In column 9, claim 15, line 15, before "the capsule but" insert --of--.

Signed and Sealed this
Seventeenth Day of March, 2015

Michelle K. Lee
*Director of the United States Patent and Trademark Office*